United States Patent
Miller, Jr. et al.

(10) Patent No.: US 12,078,555 B2
(45) Date of Patent: Sep. 3, 2024

(54) THERMISTOR BASED RESPIRATION MEASUREMENT

(71) Applicant: Telligent Metrics LLC, Dacula, GA (US)

(72) Inventors: Theodore E. Miller, Jr., Hoschton, GA (US); Kevin L Timmons, Saratoga, CA (US)

(73) Assignee: TELLIGENT METRICS LLC, Dacula, GA (US)

( * ) Notice: Subject to any disclaimer, the term of this patent is extended or adjusted under 35 U.S.C. 154(b) by 594 days.

(21) Appl. No.: 17/229,135

(22) Filed: Apr. 13, 2021

(65) Prior Publication Data

US 2021/0325260 A1    Oct. 21, 2021

Related U.S. Application Data

(60) Provisional application No. 63/054,459, filed on Jul. 21, 2020, provisional application No. 63/011,603, filed on Apr. 17, 2020.

(51) Int. Cl.
    *G01K 7/22*     (2006.01)
    *G01K 7/24*     (2006.01)

(52) U.S. Cl.
    CPC .............. *G01K 7/226* (2013.01); *G01K 7/24* (2013.01)

(58) Field of Classification Search
    CPC ........ G01K 7/226; G01K 7/24; G01K 13/024; G01F 1/69; G01F 1/696; G01F 1/698
    See application file for complete search history.

(56) References Cited

U.S. PATENT DOCUMENTS 5,061,863 A    10/1991    Mori et al.
5,069,222 A    12/1991    McDonald, Jr.
(Continued)

FOREIGN PATENT DOCUMENTS

CN    207101606 U    3/2018
WO    2015038852 A1    3/2015
(Continued)

OTHER PUBLICATIONS

Notification of International Search Report and Written Opinion of International Application No. PCT/US2021/27629 mailed on Aug. 6, 2021.
(Continued)

*Primary Examiner* — Brandi N Hopkins
*Assistant Examiner* — Janice M Soto
(74) *Attorney, Agent, or Firm* — Thomas | Horstemeyer, LLP

(57) ABSTRACT

Various examples of methods and systems related to thermistor sensing for measurement of respiration are shown. In one example, a breath sensing system includes a self-heating temperature sensor that can be positioned in respiratory air of a subject and processing circuitry that can monitor operation of the self-heating temperature sensor. Respiratory information associated with physical or physiological properties of the subject can be communicated to a remotely located computing device. Electronic switching circuitry can be included to change operation of the self-heating temperature sensor between a temperature sensing mode and a heated power dissipation sensing mode. The processing circuitry can control switching between the modes. In another example, a method includes monitoring operational conditions of a self-heating temperature sensor positioned in respired air and determining, e.g., breath velocity, breath period, breath volume, breath carbon dioxide level, and
(Continued)

heart rate based at least in part upon the operational conditions.

10 Claims, 16 Drawing Sheets

(56) References Cited

U.S. PATENT DOCUMENTS

| | | | |
|---|---|---|---|
| 5,339,687 A * | 8/1994 | Gimson | G01F 1/6965 |
| | | | 73/204.27 |
| 7,381,189 B2 | 6/2008 | Friedman et al. | |
| 8,579,829 B2 | 11/2013 | Feldman et al. | |
| 8,911,380 B1 | 12/2014 | Feldman et al. | |
| 9,131,902 B2 | 9/2015 | Halperin et al. | |
| 9,492,105 B1 | 11/2016 | Kayyali et al. | |
| 9,877,686 B2 | 1/2018 | Al-Ali et al. | |
| 10,368,807 B2 | 8/2019 | Melker et al. | |
| 10,420,490 B2 | 9/2019 | Rich et al. | |
| 10,524,696 B2 | 1/2020 | Tzvieli et al. | |
| 10,561,863 B1 | 2/2020 | Dashevsky et al. | |
| 10,576,239 B2 | 3/2020 | Zapol et al. | |
| 2001/0003922 A1 | 6/2001 | Engel | |
| 2004/0060558 A1 | 4/2004 | Gradon et al. | |
| 2005/0092078 A1 | 5/2005 | Ellis et al. | |
| 2007/0093724 A1 | 4/2007 | Nakano | |
| 2010/0004552 A1 | 1/2010 | Zhang | |
| 2010/0268105 A1 | 10/2010 | Feldman | |
| 2010/0298730 A1 | 11/2010 | Tarassenko et al. | |
| 2012/0203128 A1 * | 8/2012 | Levison | A61B 5/6819 |
| | | | 600/537 |
| 2017/0156633 A1 | 6/2017 | Travis et al. | |
| 2018/0020976 A1 | 1/2018 | Yossi | |
| 2018/0256070 A1 * | 9/2018 | Garvey | A61B 5/091 |
| 2019/0240432 A1 | 8/2019 | Burgess et al. | |
| 2019/0282180 A1 | 9/2019 | Babaeizadeh | |
| 2019/0362822 A1 | 11/2019 | Haveri et al. | |

FOREIGN PATENT DOCUMENTS

| | | |
|---|---|---|
| WO | 2016110804 A1 | 7/2016 |
| WO | 2017199089 A2 | 11/2017 |
| WO | 2010015865 | 3/2018 |

OTHER PUBLICATIONS

Qudsi, "Low-cost, thermistor based respiration monitor", 2013 29th Southern Biomedical Engineering Conference. IEEE.

Bhattacharya, et al. "Real time android app based respiration rate monitor", International Conference on Electronics, Communication and Aerospace Technology, 2017.

EP Search report for EP 21787911 mailed Apr. 17, 2024.

* cited by examiner

INHALED AIR

THERMISTOR BASED RESPIRATION MEASUREMENT

CROSS REFERENCE TO RELATED APPLICATIONS

This application claims priority to, and the benefit of, U.S. provisional application entitled "Thermistor Sensor Method for the Measurement of Respiration" having Ser. No. 63/011,603, filed Apr. 17, 2020, and U.S. provisional application entitled "Thermistor Based Respiration Measurement" having Ser. No. 63/054,459, filed Jul. 21, 2020, both of which are hereby incorporated by reference in their entireties.

BACKGROUND

In many situations, the ability to non-invasively monitor respiration offers many benefits. Thermistors are versatile metal oxide semiconductors that exhibit non-linear resistances with temperature, used primarily for temperature measurements. In addition to measuring temperatures, with requisite support circuitry they can self-heat and thus measure flow rate via thermal dissipation. Thermistors are available in a wide range of sizes, down to thermistor "flakes" weighing as little as 50 micrograms. Previously, separate thermistors operating in different self-heating and ambient temperature sensing modes have been used.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
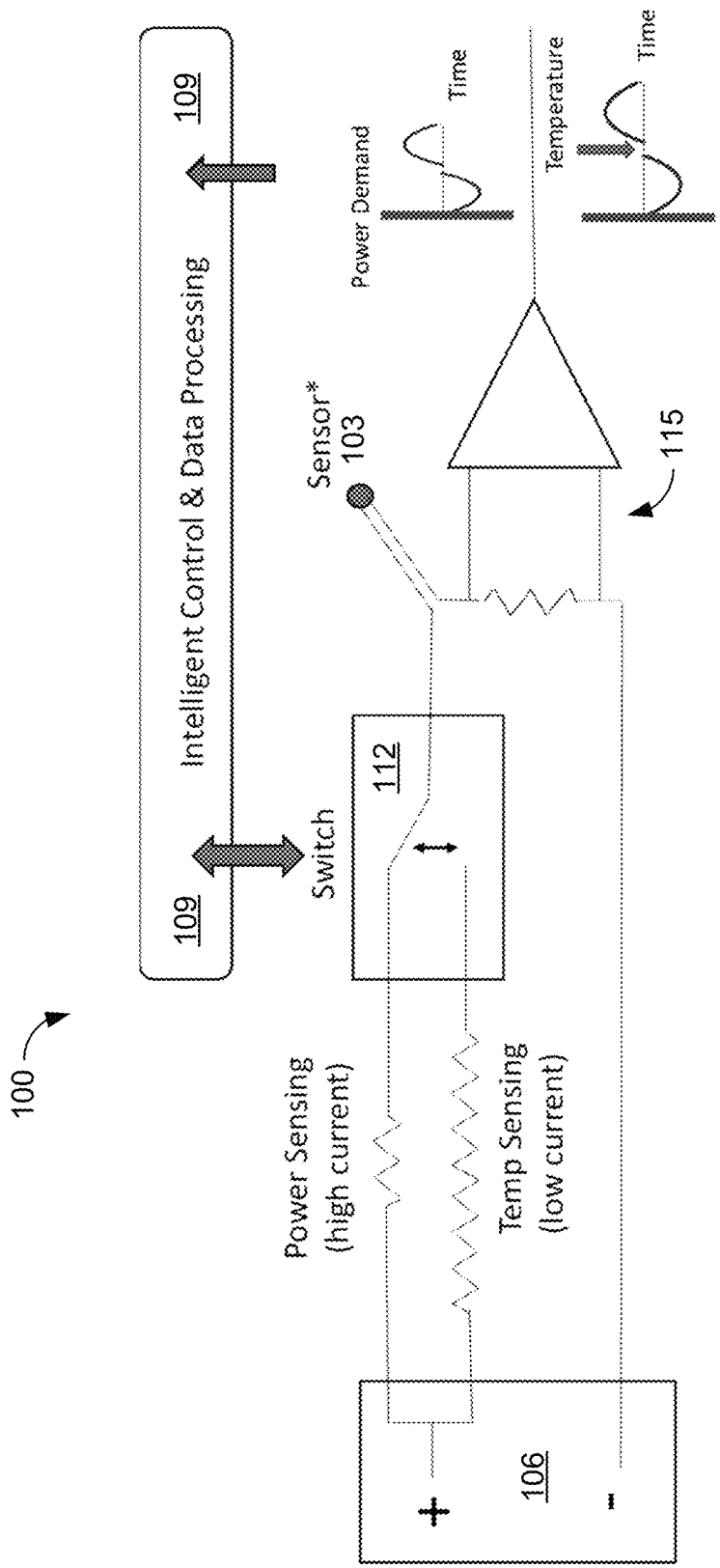
FIGS. 1 and 2 are schematic diagrams illustrating examples of respiratory measurement circuitry utilizing a single thermistor, in accordance with various embodiments of the present disclosure.

Disclosed herein are various examples related to thermistor sensing methods and systems for measurement of respiration. For example, a single very tiny thermistor affixed to a respiratory mask can be used to measure breath temperature trends, breath rate (flow cycles), breath velocity, single-breath volume (e.g., by measuring flow rate, breath time, and assuming a certain flow velocity profile over the mask area), and respiration efficiency ($O_2/CO_2$ exchange). While the use of a single thermistor for the determination of these variables is described in this disclosure, it should be understood that other semiconductor sensing devices capable of both self-heating and independently sensing temperature can also be used in place of the thermistor as would be understood in the context of this disclosure. The combination of all these from the same sensor, offers special diagnostic advantages. The medical utility of this product is to integrate these parameters together and employ patient-specific algorithms to infer and predict health conditions in real time. Reference will now be made in detail to the description of the embodiments as illustrated in the drawings, wherein like reference numbers indicate like parts throughout the several views.

In addition to temperature sensing, thermistors can be used as fluid flowmeters by sensing the amount of power needed to maintain a fixed, elevated sensor temperature. The higher the flow, the more power is needed to compensate for the higher heat loss. A single thermistor, with appropriate electronic control circuitry, can be used to measure both the temperature and fluid flow. Using this configuration, the single thermistor can be used to measure breath temperature, breathing rate, maximum breath velocity, single-breath volume, and/or $O_2$ to $CO_2$ respiration efficiency. In some embodiments, the single thermistor and, optionally, at least some of the electronic circuitry can be, for example, affixed to a respiratory mask or positioned within a tube leading from a respiratory mask to be in the flow of the exhaled air.

Thermistors are available in a wide range of sizes, down to "flakes" weighing as little as a few micrograms. Using a thermistor with a low mass affords two essential advantages: rapid speed of response and low power requirements. Micro-thermistors can be switched extremely rapidly from mode to mode to perform these duties as will be discussed. The micro scale of the thermistor also makes the power requirement low enough to devise a small lightweight mask attachment that could sense all these variables and transmit the results wirelessly (e.g., through a Bluetooth® or other appropriate wireless link). For example, a miniature battery, solar cell or other appropriate power source may be used on a mask to supply power for the sensor and interfacing circuitry.

Referring to FIG. 1, shown is a schematic diagram illustrating an example of single thermistor 103 with sensing and control circuitry 100. A supply voltage 106 can be switched between a self-heated power dissipation sensing mode where a high current is supplied through the thermistor 103 and a temperature sensing mode where a low current is supplied through the thermistor 103. As illustrated, intelligent control and processing circuitry 109 can control the modes via switch 112 (e.g., a solid state switch or other appropriate switch), which can select between the power dissipation and temperature sensing modes. The heated power dissipation sensing mode can track the pattern of power needed to hold the thermistor at a high temperature, e.g., in a range from about 250 degrees C. to about 300 degrees C. A sensing circuit 115 can be used to monitor the power demand of or current flow through the thermistor 103 (e.g., voltage drop across a calibrated sensing resistor that can be amplified for sensing) by the intelligent control and processing circuitry 109. Processing of the sensed signal can provide feedback control information which can be used by the intelligent control. Data processing can also provide one or more variables: breath temperature, breathing rate, maximum breath velocity, single-breath volume (in and out), or $O_2$ to $CO_2$ respiration efficiency, as will be discussed. On-board computations can calibrate the system and optimize accuracy, exploiting physiological interrelationships among the variables.

Figure 2:
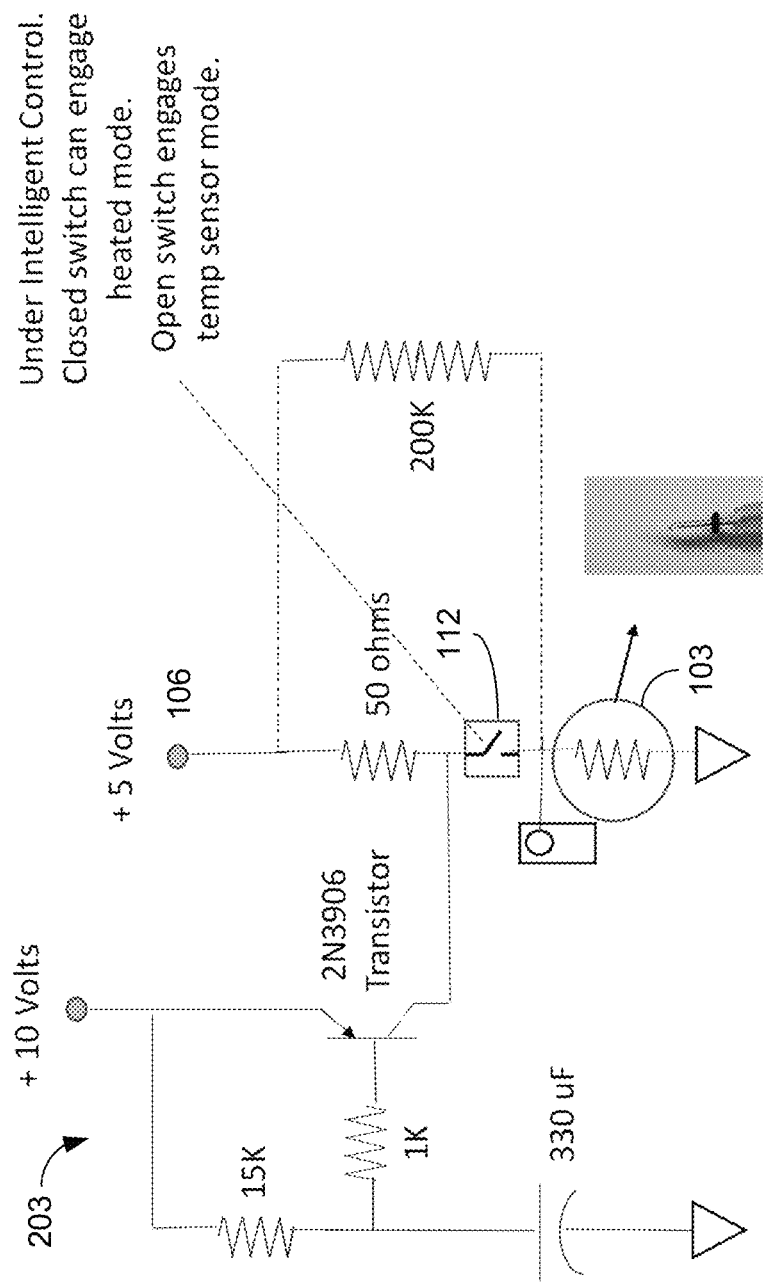
Figure 3A:
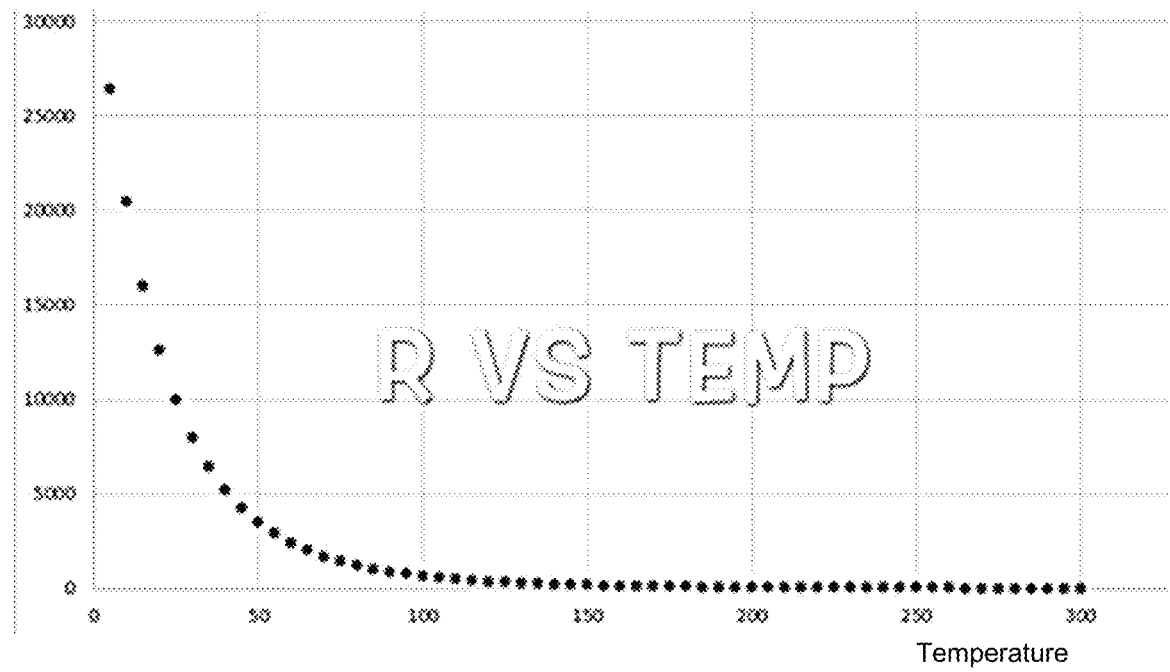
FIGS. 3A and 3B illustrate examples of the resistance and peak power variations for the thermistor leading to the measurement circuitry of FIGS. 1 and 2, in accordance with various embodiments of the present disclosure.
Figure 3B:
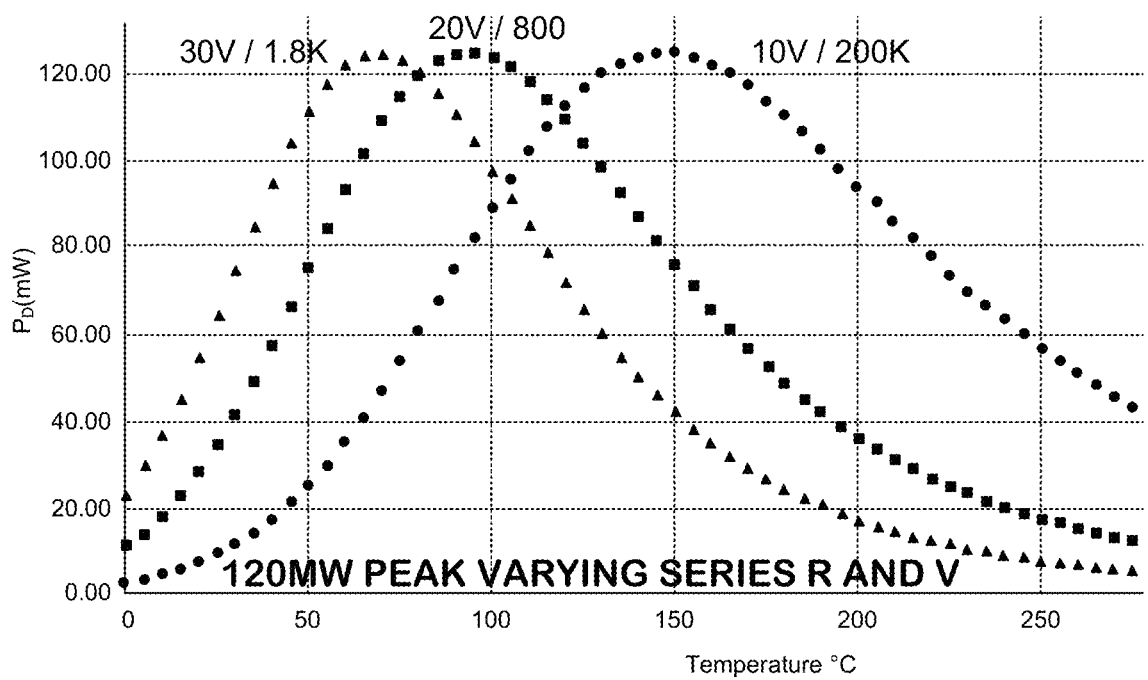

FIG. 2 shows an example of the operating circuitry for the two modes. In this implementation, the switch 112 is closed in the power dissipation sensing mode to allow current from the 5V supply voltage 106 to flow through the thermistor 103 via a 50 Ohm resistor. An image of a microthermistor (e.g., a Fenwal GB38P12, 9.1 kOhms at 20 degrees C., −4% per degree C., dissipation constant of 0.4 mW per degree C.) that can be used is provided as an inset of FIG. 2. FIG. 3A illustrates an example of the resistance variation with temperature. The supply voltage 106 and resistance can be chosen to maintain the thermistor at a desired operational temperature (e.g., at 260 degree C.). FIG. 3B illustrates the effect of varying series resistance and voltage on the power dissipated at the thermistor. For the circuit in FIG. 2 with a Fenwal GB38P12 thermistor 103, the voltage stabilizes at 2.12 V at room temperature. From V=iR and a thermistor resistance (R) of 37 Ohms, the power loss (P=$i^2$R) is 122 mW.

Returning to FIG. 2, the operating circuitry can, optionally, include a startup circuit 203 that can be operated to trigger the thermistor 103 into a self-heat mode. The transistor can be activated to start the thermistor heating and is deactivated after a predefined heating period (e.g., 0.1 second), e.g., by an RC timing circuit on the base of the transistor. The negative temperature coefficient of the thermistor 103 stabilizes the high temperature.

Figure 3C:
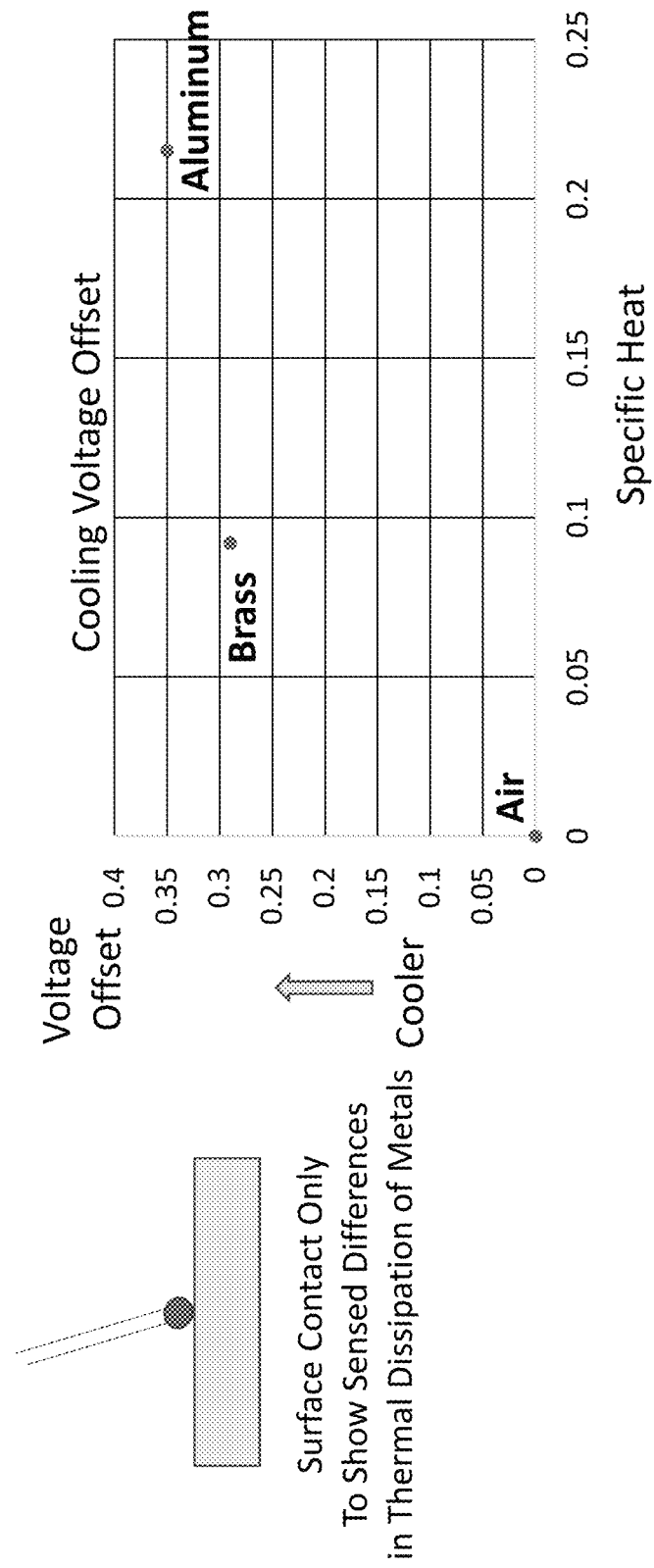
FIGS. 3C and 3D illustrate examples of differences between thermistor thermal dissipation, in accordance with various embodiments of the present disclosure.
Figure 3D:
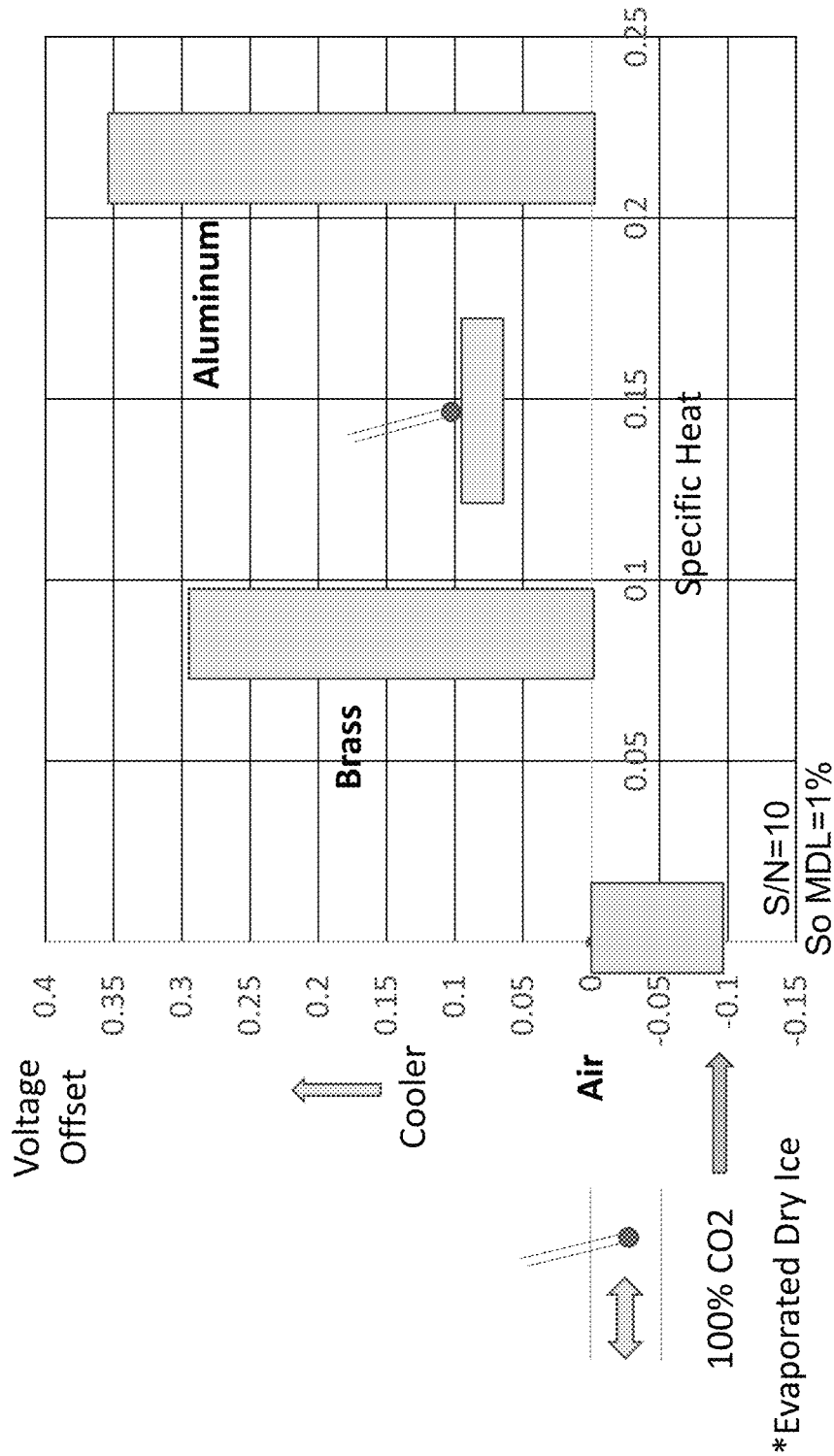

In the temperature sensing mode, the switch 112 is opened to allow a reduced or lower current to flow from the 5V supply voltage 106 through the thermistor 103 via a 200 Ohm resistor. At the lower current, the thermistor 103 will cool. The thermal dissipation will vary with the medium contacting the thermistor 103. The cooling effect of the medium increases as the specific heat increases. For example, a thermistor cools faster when in contact with aluminum than when in contact with brass or surrounded by dry air. FIG. 3C illustrates differences between the thermal dissipations. When the thermistor 103 is positioned or immersed in the respiratory air flow path, the composition of the air being inhaled and exhaled will affect the thermal dissipation which can be measured through the sensing circuit 115. FIG. 3D illustrates the effect of $CO_2$ on the comparative response. As the resistance of the thermistor 103 changes from dissipation of the stored heat, the current flow through the thermistor 103 and thus the voltage across the sensing resistor will vary in an identifiable fashion.

Figure 4A:
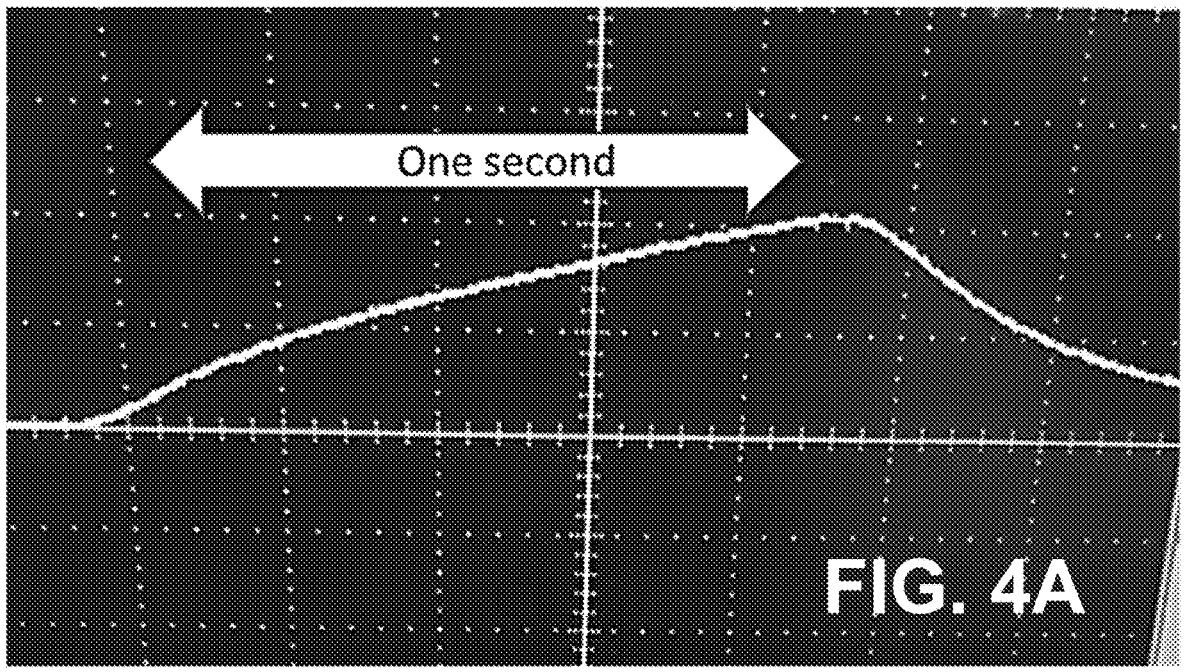
FIGS. 4A and 4B illustrate examples of trace responses to breath over a thermistor in a constrained flow path and in open air, in accordance with various embodiments of the present disclosure.
Figure 4B:
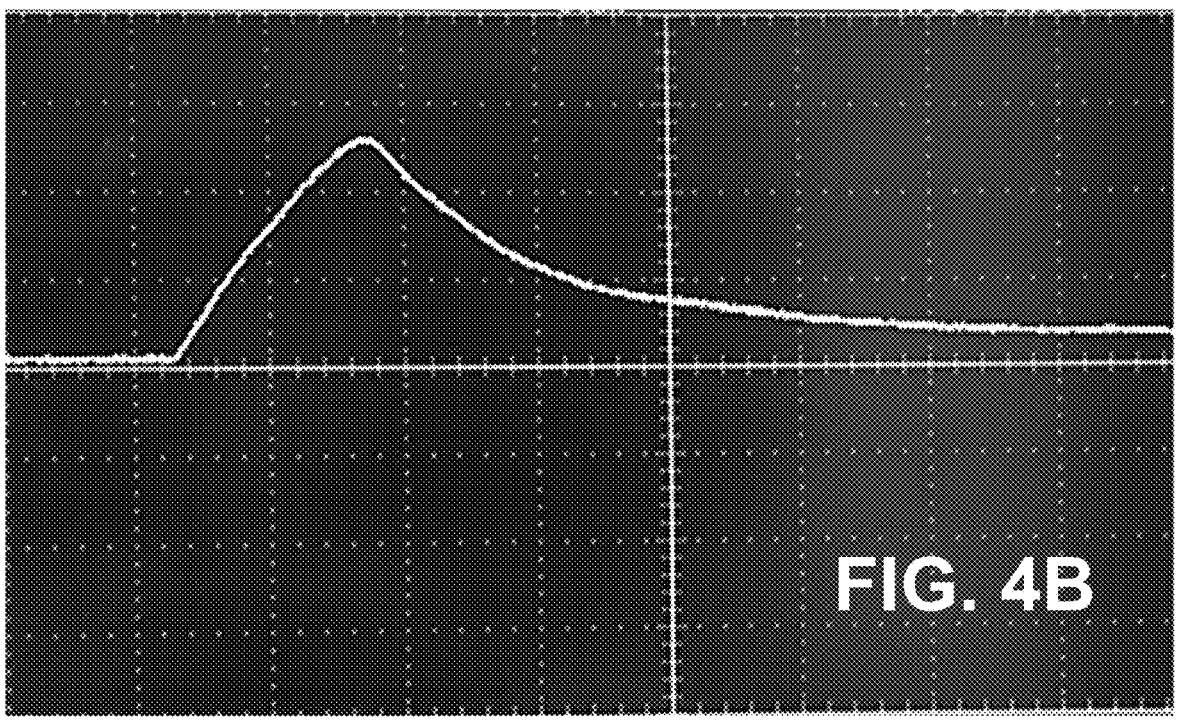

FIG. 4A shows an example of a trace response to breath over a thermistor 103 that is centered within a flow block hole (1.60 mm ID×38.1 mm length) to constrain the airflow. The thermistor 103 is self-heated to a resting temperature of 260 degrees C., which correlates to a baseline sensing voltage of 2.1 V. As the breath is blown over the thermistor 103, its resistance varies in response to the cooling effect causing the sensed voltage to increase as shown (trace settings were set to 0.5 V/div along the vertical axis and 250 msec/div along the horizontal axis. The breath stops at the peak of the trace. Once the airflow over the thermistor 103 stops, the self-heating of the thermistor 103 causes the sensed voltage to return to the baseline sensing as the resistance changes. The recovery time is about 0.5 second. Both transitions are affected by the airflow over the thermistor 103 and the thermal dissipation properties of the gas being blown over the thermistor 103. A similar response is produced by blowing on a thermistor 103 in open air (without a defined flow path). The response waveform is similar to that shown in FIG. 4A and exhibits the same recovery decay time during self-heating.

Figure 5A:
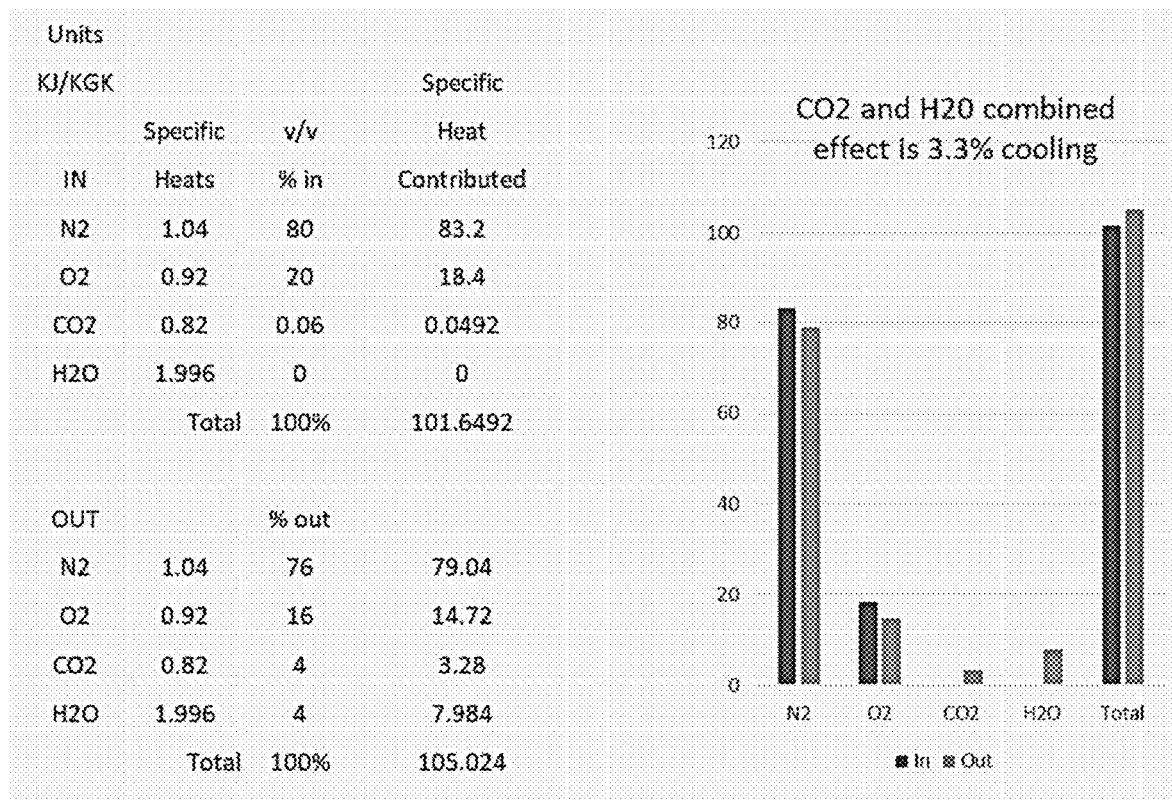
FIGS. 5A-5C illustrate the effects produced by the different gas compositions of inhaled air and exhaled breath, in accordance with various embodiments of the present disclosure.

When an individual exhales, three main parameters change from the inhaled air to the exhaled breath: temperature (an increase by about +6.7 degrees C.); humidity (water content increases from almost nothing to about 5%); and carbon dioxide (an increase from almost nothing to about 4%). Lung tissues are made up of about 80% water and thus maintain a surprisingly constant exhaled humidity level (about 4% v/v water) and temperature (about 34.4 degrees C.). The effect of the different gas compositions of the inhaled air and exhaled breath is illustrated in FIG. 5A. The differences in the composition between the typical inhaled air and exhaled breath is graphically illustrated in the bar chart on the right. Air is a relatively simple type of mixture: the main ingredient, at about 80% by volume (v/v), is nitrogen; next is oxygen at around 20%, followed by argon, 1%, and water vapor, at varying levels, maximally at about 2%. Atmospheric carbon dioxide is at 600 ppm by volume but rises to as high as 4% (40,000 ppm) in expired air.

As can be expected, the amount of $O_2$ has been reduced in the exhaled air and $CO_2$ and $H_2O$ have been added. The specific heat contribution of the different gas concentrations is shown in the tables in FIG. 5A. The effect of different gas concentrations is a 3.3% difference in cooling between inhalation and exhalation. The effect on the thermistor cooling is visible in the trace responses of FIGS. 5B (inhaled air) and 5C (exhaled breath). A 48.25 cm length of 1.93 cm PVC pipe was used with the thermistor 103 positioned in a well 7.5 cm from the exit end to measure the responses to inhalation and exhalation.

The effect of ambient temperature variations was also examined. By heating the thermistor 103 to 250 degree C. and allowing the thermistor to reach equilibrium, the voltage response of the thermistor was measured using the sensor circuit 115 and plotted in FIG. 6. As can be seen, increased ambient temperatures reduces the voltage across the sensing resistor in a predictable fashion. This shows that the measured effect of ambient temperature on the baseline voltage of the heated sensor in this voltage divider circuit may be estimated as a linear −10 mV/degree F. As such, the elevated lung exit temperature of 94 degree F. compared to 74 degree F. should lower the output trace by 200 mV, i.e. (−10 mV/degree F.)×20. But it has no observable effect on the breath measurements of FIGS. 5B and 5C. This may be attributed to the long response time needed to equalize with ambient temperature. The 33.3 degrees C. breath has minimal effect during the timeframe of a single breath.

Figure 5B:
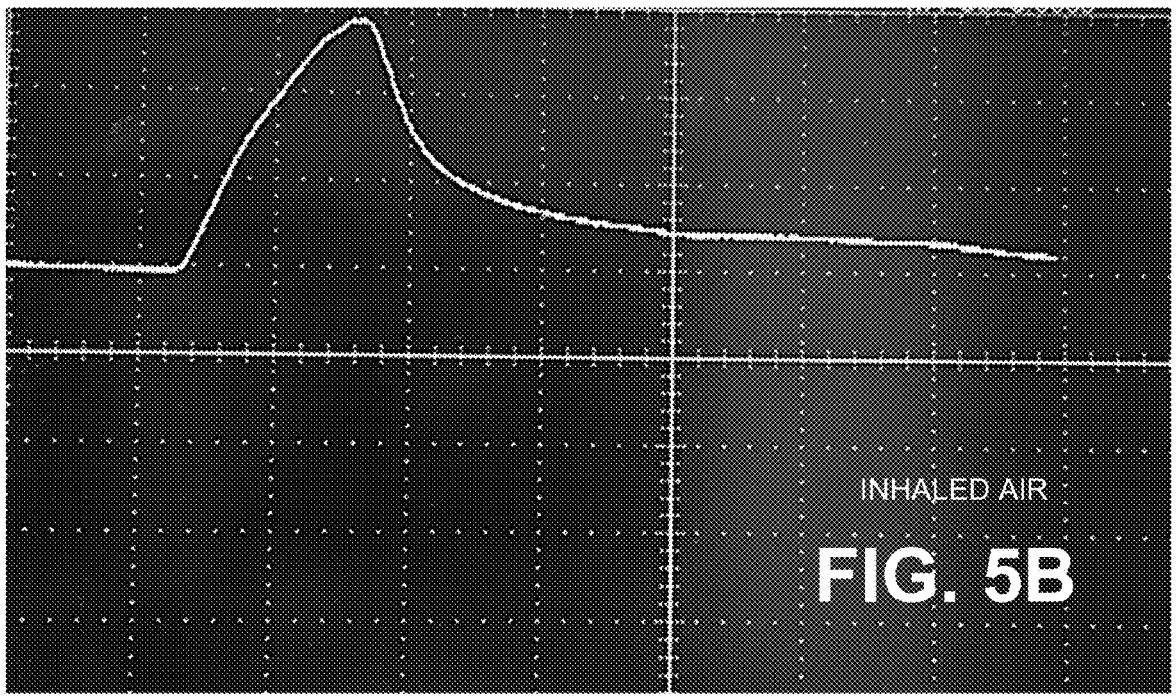
Figure 5C:
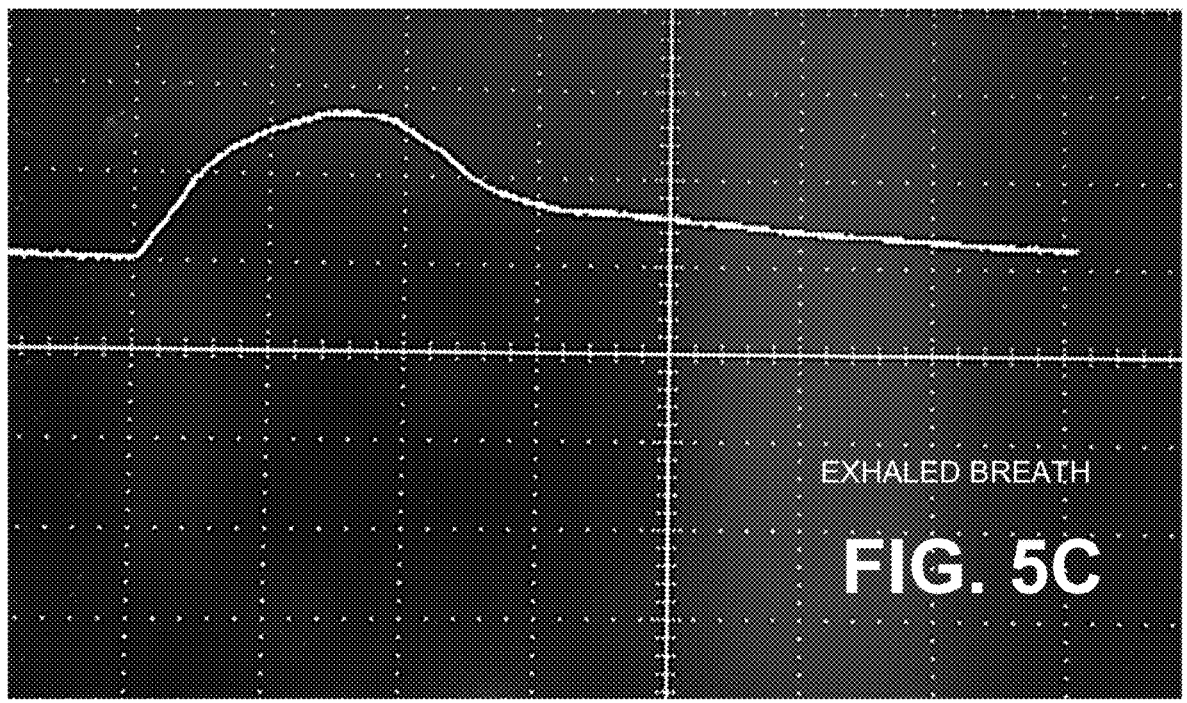
Figure 6:
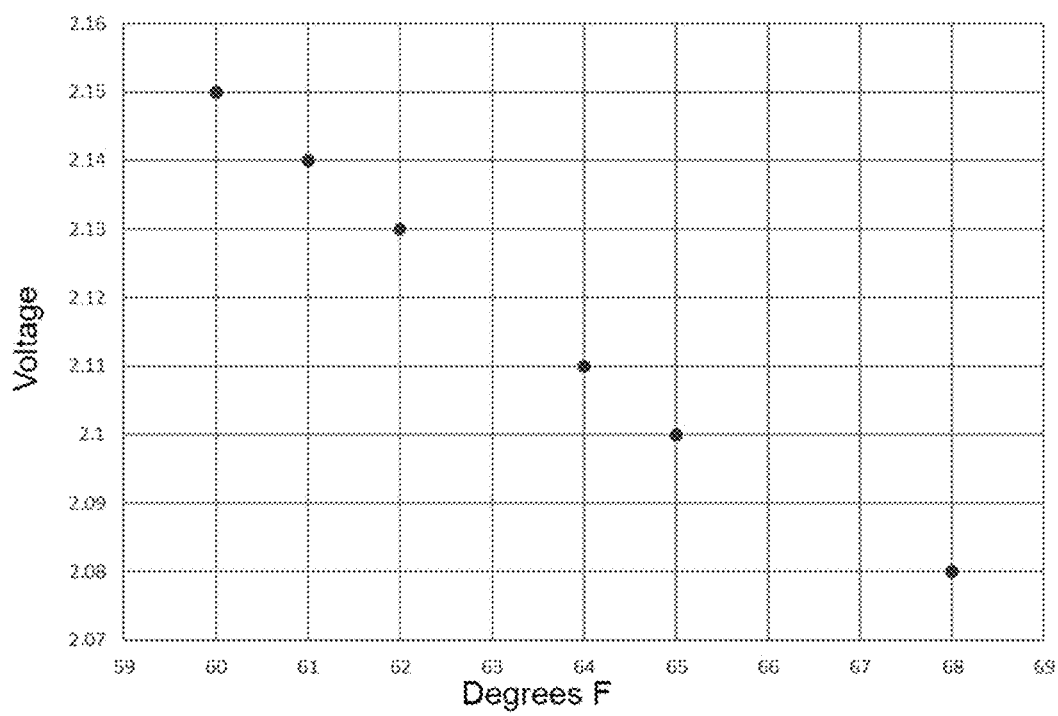
FIG. 6 illustrates the effect of ambient air temperature variations, in accordance with various embodiments of the present disclosure.
Figure 7:
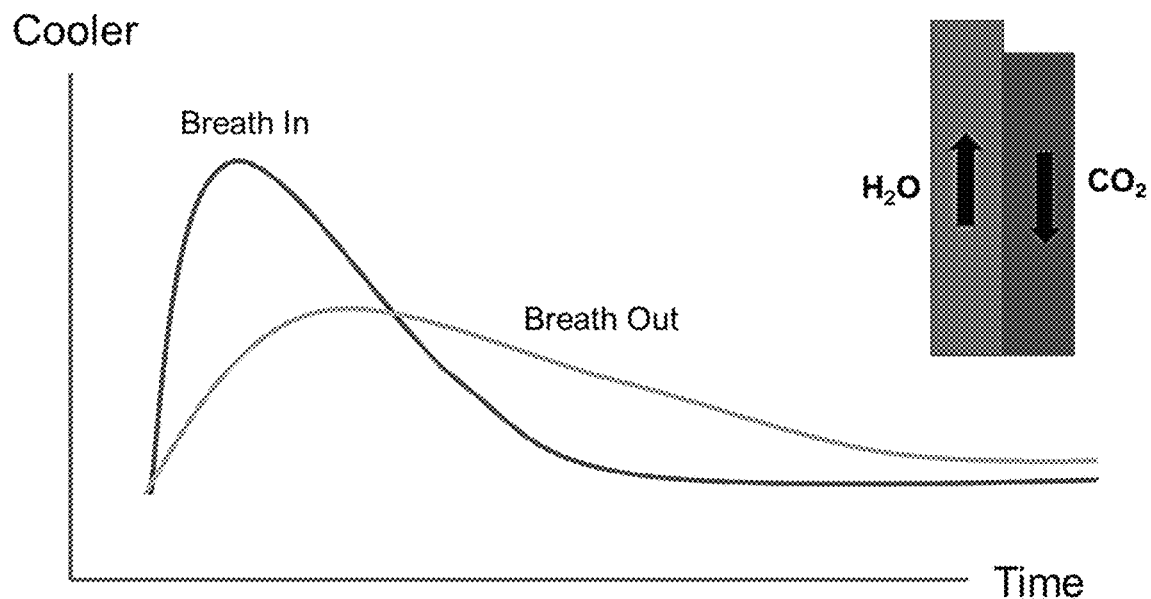
FIG. 7 illustrates the effect produced by the water vapor and carbon dioxide of inhaled air and exhaled breath, in accordance with various embodiments of the present disclosure.

As illustrated in FIG. 5A, the percent levels of water vapor and carbon dioxide weighted by their specific heats, contribute +8.0 and −3.3, respectively, to the heat dissipation on a proportionate basis in exhaled breath. Comparing voltage baselines at the stopped-flow times of inhaled air and exhaled breath will reveal the level of carbon dioxide by difference. In other words, water vapor (specific heat×its % amount) will drive the voltage more positive than the carbon dioxide will drive it down, by a factor of 8.0/3.3, as shown in FIG. 7. The measured results of FIGS. 5B and 5C are consistent with the predicted effect in FIG. 7.

Consider that the heated thermistor 103 detects the heat drawn from it. Water vapor draws heat whereas $CO_2$ tends to insulate, which counteracts each other. Water draws heat about twice as much as $CO_2$ insulates. But lungs are made of about 80% water, so the air dwell-time in the lungs (which can also be measured) determines the water amount in the exhaled breath. Since this can be predicted, the amount of carbon dioxide can be found. During testing, it was found that there was a −90 mV change for 100% $CO_2$ exposure. So, the 4% concentration of $CO_2$ should give −3.60 mV=−90 mV×(4/100). As indicated in FIG. 5A, a net cooling of 3.3% is expected from the combined effects of $H_2O$ and $CO_2$, and the relative contributions of $O_2$ and $CO_2$ are 8.0/3.3. So, if $CO_2$ produces a −3.6 mV change, $O_2$ then gives +5.1 mV or a baseline offset of +5.1 mV should be seen. If the water vapor holds constant, then any drop in $CO_2$ would increase the offset from 5.1 mV in a linear fashion. For example, a drop to 2% $CO_2$ would give a reduction in the $CO_2$ effect of 1.8 mV (=3.6/2) instead and an offset of 6.9 mV. Thus, with constant water level, the change in % $CO_2$ ($\Delta$% $CO_2$) from 4% can be estimated as −0.90 mV/$\Delta$% $CO_2$.

Figure 8:
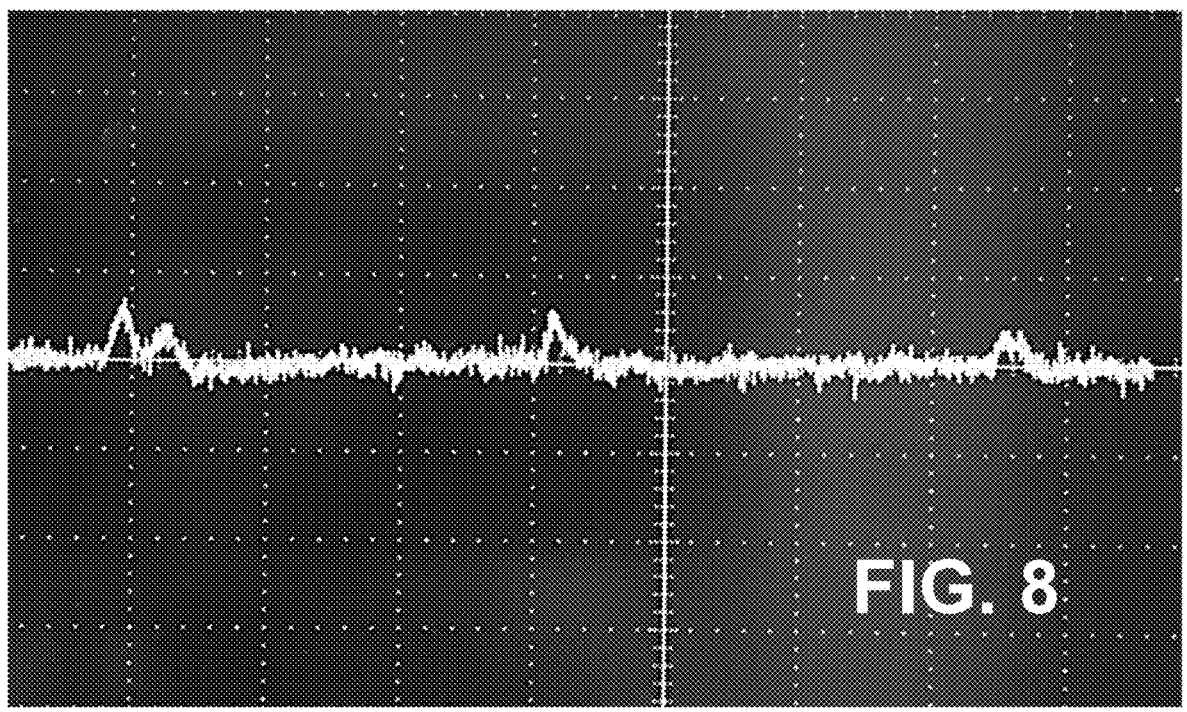
FIG. 8 illustrates an example of the effect resembling heartbeat, in accordance with various embodiments of the present disclosure.

It may also be possible to detect heartbeat using the sensing circuitry. Beating of the heart can affect the lung volumes which can produce small variations air flowing into or out of the lungs. FIG. 8 shows a trace response representing variations in the monitored voltage that can be produced by a beating heart. Detection of the heartbeat may be most effective during quiet periods between breaths since the effects of lung motion during inhalation and exhalation may overwhelm the heartbeat indications.

Figure 9:
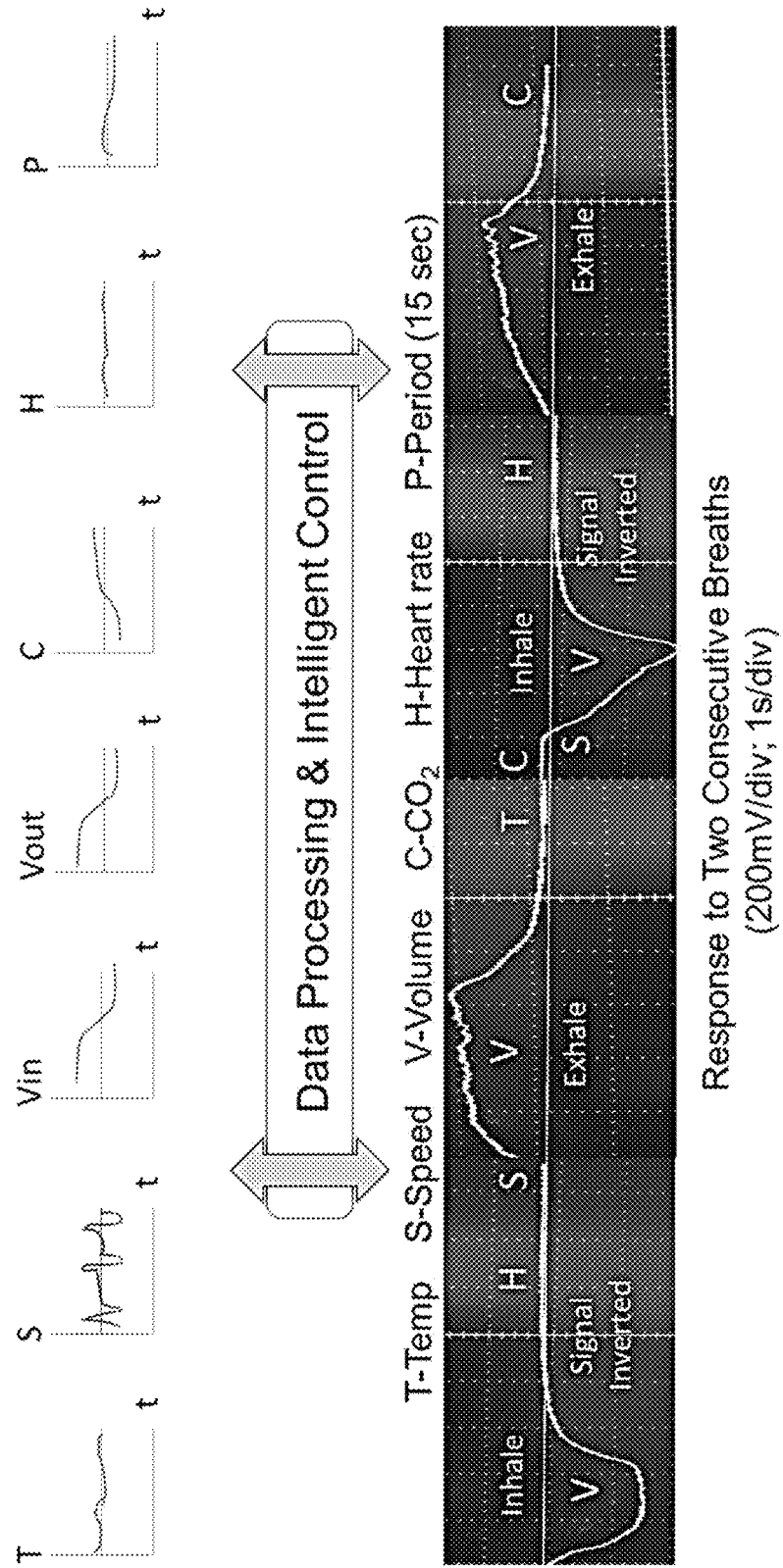
FIG. 9 illustrates an example of a recorded response and respiration information that can be derived from it, in accordance with various embodiments of the present disclosure.

Discussion of the data processing and controls provided by the intelligent control and processing circuitry 109 will now be discussed with respect to FIG. 9. Shown in FIG. 9 is an example of a trace response for two consecutive breaths. The information extracted from the measured response can be processed by the intelligent control and processing circuitry 109 to evaluate temperature (T) of the fluid flowing past the thermistor 103, speed (S) of the fluid flow, volume of the fluid (both inhaled and exhaled −Vin and Vout), the carbon dioxide (C) being exhaled, the heart rate (H) and the respiration period (P). The relationship between the sensor signal and the information for each evaluation is indicated on the trace response.

Temperature (T). Thermistors are commonly used to measure temperature, but in a non-self-heating mode. The intelligent control and processing circuitry 109 can decide how often to switch to the temperature sensing mode since as the data shows, the tiny sensor can cool very rapidly in order to achieve equilibrium. Ambient air and breath temperatures reflect not only body temperature but also allow corrections of the amount of water in exhaled breath, fine tuning the finding of the level of carbon dioxide by difference, as described later. The micro size allows switching to detect the ambient temperature at zero air flow during breath direction reversal to allow tracking inhaled and exhaled lung temperatures, and thus to infer body temperatures. This is illustrated in FIG. 1, where the temperature sensing can take place during the pause between exhalation and inhalation. The quiescent periods naturally occur twice per breath cycle, and thus can infer body temperature in a manner typical of thermistors. The intelligent control and processing circuitry 109 can determine the temperature based upon the measured data and provide the results for display to a user.

Speed of breath (S), or maximum velocity. The slope of the sensed signal is monotonically changing with the velocity of air over the thermistor 103, and is highly variable, as is breath. The speed of breath or maximum velocity can be used as an indicator of health, separate from exhalation volume. Note that the AC-coupled or derivative mode shows in a sensitive way, how this varies. Inhalation speed is less variable than exhalation speed, due to the fact that atmospheric pressure drives inlet flow past the thermistor 103 (e.g., through a constrained passageway such as a small tube), whereas lung constriction dynamics control outgoing flow and are thus more variable and informative. The velocity of the fluid flow can be measured by holding the thermistor's temperature at a high level and then tracking the power needed to maintain that temperature based upon the sensed voltage. The higher the flow rate, the greater the removal of heat energy and the greater the demand for heat, as sensed.

Volume (V). Through a flow channel, the average speed, or velocity, of flow, multiplied by the flow cross sectional area and elapsed time yields volume. In the case of a sensor on a mask, the placement of the velocity sensor within the mask area should be managed. There will be a flow velocity distribution pattern over the mask surface, which affects the fluid flow past the thermistor 103. The mask design can be adapted to make this distribution essentially uniform or can focus a controlled amount of flow past the sensor. Once this pattern is known, the velocity sampled in a certain position can be used to calculate the average velocity and then this amount multiplied by time yields the total volume transferred in or out over that period.

Inhalation and exhalation breath volumes should be equal, which can provide a self-correcting measurement for the intelligent control and processing circuitry 109. But, significantly, slight differences in their thermal dissipation characteristics would make them appear to differ a bit. As explained, the exhaled breath is expected to be more heat-conductive due to added water vapor, and thus to cool the sensor slightly, raising the voltage and thus increasing slightly the velocity reading due to this compositional difference, enlarging the estimate of exhaled volume. This can be exploited by using an operating algorithm that combines results from these multiple parameters, adding to the accuracy of the measurement of water, and, in turn, the measurement of carbon dioxide.

$CO_2$ (C). Three major variables are different in the exhaled air: temperature, water, and carbon dioxide. Temperature can be measured directly. Water and carbon dioxide affect thermal dissipation in opposite directions. But the water amount is generally consistent and can be adjusted further from the temperature and dwell time in the lungs (which can be determined from the power demand pattern). So, the level of $CO_2$ can be determined based upon the quiescent baseline offset as well as from the apparent difference in volume, inhalation vs. exhalation.

Heart Rate (H). In the twice-a-cycle moments of resting time, the lungs are slightly jostled by heartbeats. In the self-heated power dissipation sensing mode, the thermistor is extremely sensitive and can detect the subtle air flow pulse when AC coupled and amplified as shown in FIG. 8. These slight variations can be detected and processed to determine the heartrate.

Period (P) or breathing rate. The breathing rate can be determined from the power demand pattern as illustrated in FIG. 1. A single period of respiration includes inhalation of air and exhalation of breath, both of which increase the power demand as the fluid flows past the thermistor 103. The breath events are easily seen, so that the total time for a cycle is simply the period of breathing. By tracking the cycles of the power demand, the frequency or rate of breathing can be determined by the intelligent control and processing circuitry 109. The number of these within a minute, is the breath rate.

Sensor Electronics Interface. The intelligent control and processing circuitry 109 can comprise processing circuitry (e.g., including a microprocessor and memory). The intelligent control and processing can be implemented in hardware, software, firmware, or a combination thereof. For example, the intelligent control and processing can be implemented in software or firmware that is stored in a memory and that is executed by a suitable instruction execution system. If implemented in hardware, as in an alternative embodiment, the intelligent control and processing can be implemented with any or a combination of: a discrete logic circuit having logic gates for implementing logic functions upon data signals, an application specific integrated circuit (ASIC) having appropriate combinational logic gates, a programmable gate array (PGA), a field programmable gate array (FPGA), etc. The intelligent control and processing circuitry 109 can also include a communication interface that can transmit (e.g., wirelessly through a Bluetooth® or other appropriate wireless link) information to a remotely located device (e.g., computing device or user device such as, but not limited to, a laptop, tablet, smartphone, smartwatch, etc.). A power supply (e.g., battery, solar cell, or other appropriate supply) can be included to provide power to the intelligent control and processing circuitry 109. Low energy circuitry can be utilized to extend the life of the power supply.

The intelligent control and processing circuitry 109 can be configured to monitor the voltage across the sensing resistor of the sensing circuit 115 (FIG. 1). For example, the voltage can be converted into an appropriate format by the intelligent control and processing circuitry 109 and transmitted to a remotely located computing device for further processing to determine features of the monitored respiration. In some embodiments, the intelligent control and processing circuitry can utilize machine learning, neural networks or other trained artificial intelligence in the monitoring and control of the system. The intelligent control and processing circuitry 109 can also be configured to control operation of switching between the operational modes. For example, the intelligent control and processing circuitry 109 can monitor power demand by the thermistor 103 and use that control switching between temperature sensing and power dissipation sensing modes during the quiescent periods during breaths. In some embodiments, the intelligent control and processing circuitry 109 can process the sensed data and send the results to a user device (e.g., smart phone, tablet, computer, etc.) for display. The intelligent control and processing circuitry 109 may also comprise an interface that can provide information directly to a user. For example, the intelligent control and processing can monitor airflow through the face mask and provide feedback (e.g., through a display device such as, e.g., an LED) regarding the fit of the mask based upon changes in the monitored air flow at that position. The relationship between the overall airflow through the mask and the airflow at the monitored position can be utilized to determine the level of fit. An indication regarding the level of fit may be provided.

Figure 10A:
FIGS. 10A-10E illustrate examples of applications of the thermistor based respiration measurement system, in accordance with various embodiments of the present disclosure.
Figure 10A:
Figure 10B:
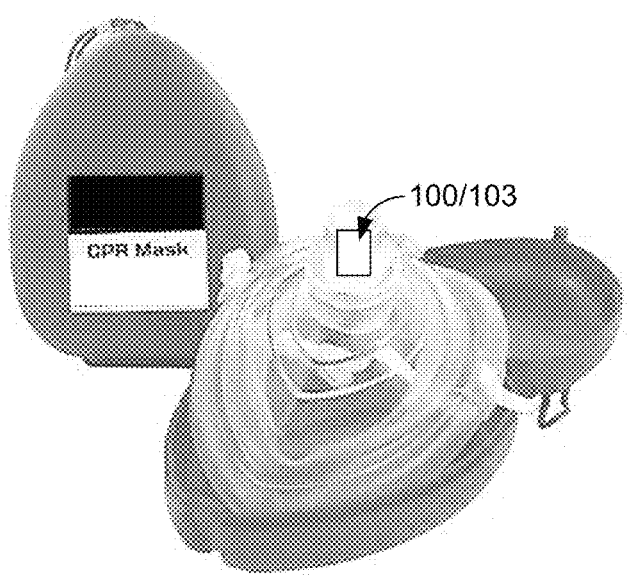
Figure 10C:
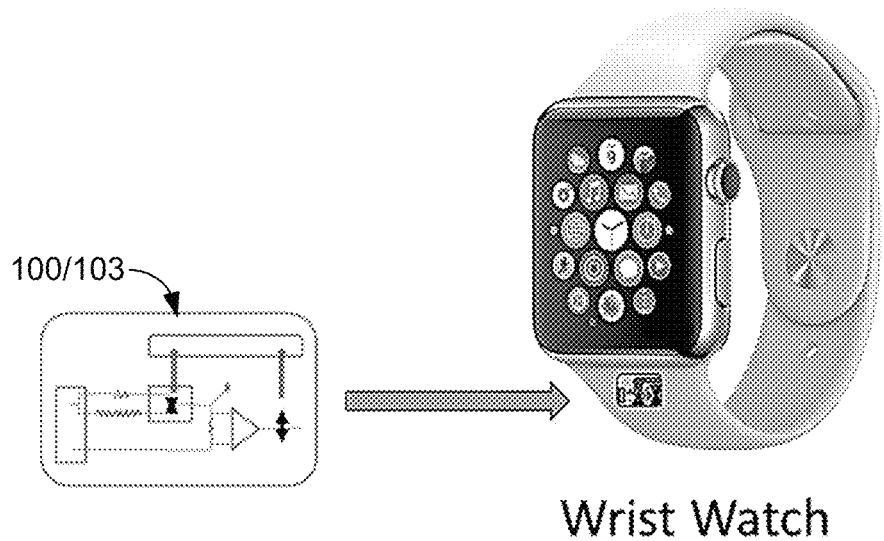

The medical utility of this product would be to integrate these parameters together and be able to use patient-specific algorithms to infer and predict health conditions in real time. The single thermistor-based sensing system can be applied to a wide range of applications. For example, the thermistor can be located in a flow tube of a mask or cannula as illustrated in FIG. 10A. The fluid flow would be directed past the thermistor 103 by the tubing. The single thermistor-based sensing system can also be utilized in other masks such as, e.g., a CPR mask as shown in FIG. 10B. The thermistor can be incorporated into the connection of the mask, which allows it to be used with any available air connection. This configuration can provide critical information about circulation and ventilation before, during and after CPR. In some embodiments, the single thermistor-based sensing system can be implemented as part of a wristwatch (e.g., a smartwatch) such as illustrated in the example of FIG. 10C. The sensing system can be positioned on a wristband, where the user can breathe on the thermistor and the analysis results may be displayed on the watch itself.

Figure 10D:
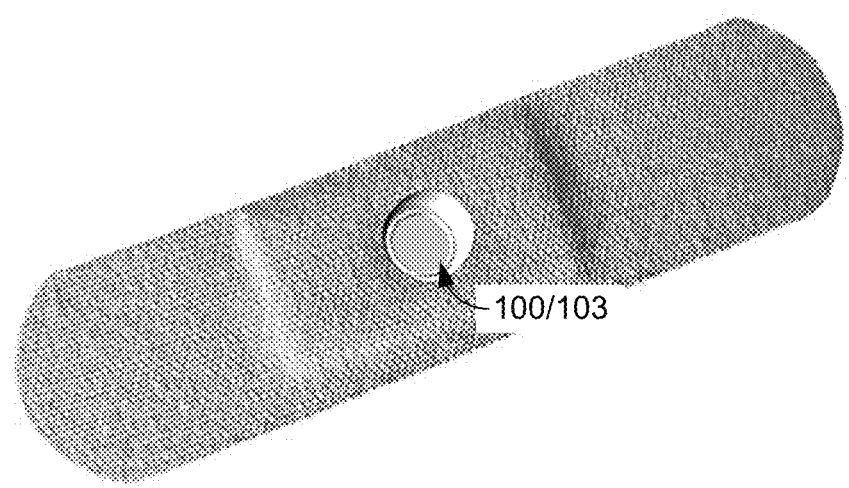
Figure 10E:
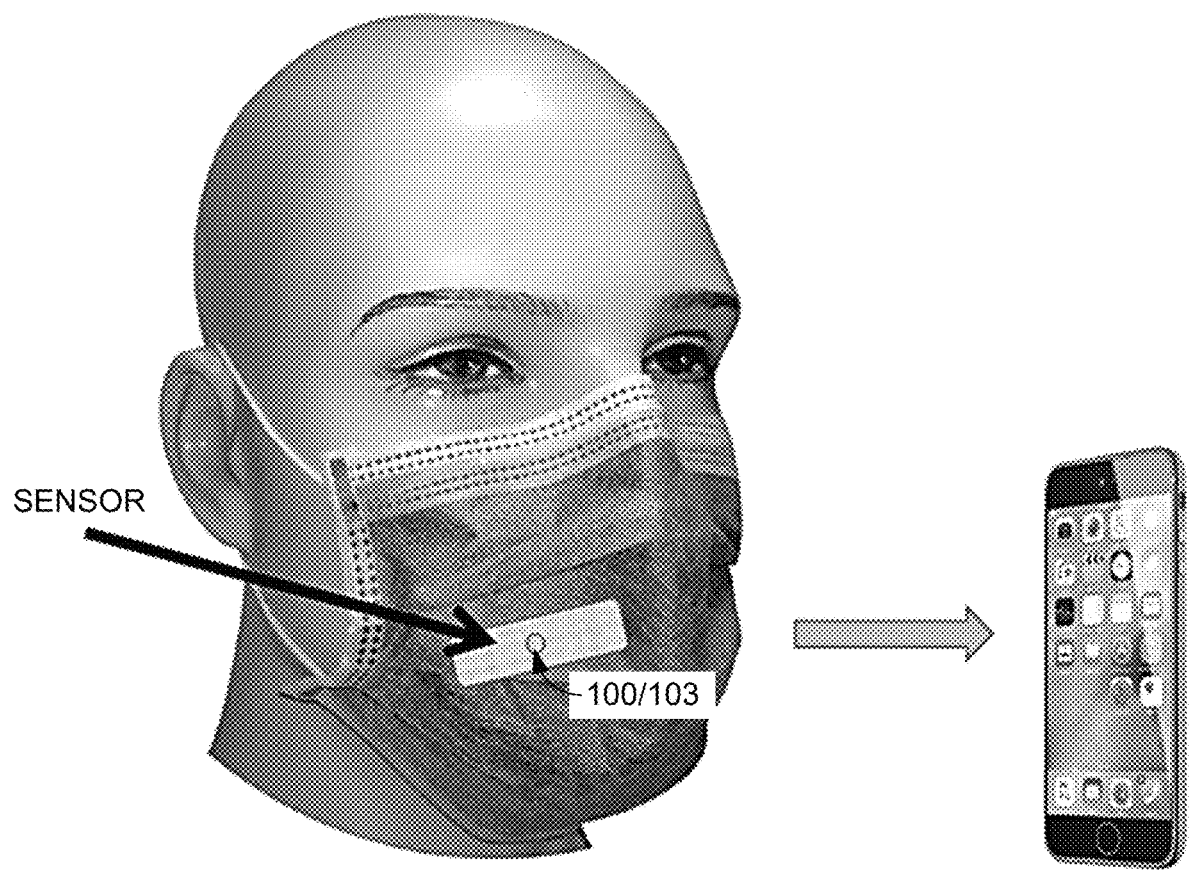

The single thermistor-based sensing system can also be used with traditional disposable facial masks. The thermistor sensor can be secured to the face mask using, e.g., a tape mounted system or other adhesive or appropriate affixing methods. FIG. 10D illustrates a simple tape mounting system where the thermistor 103 is mounted to a pad supported by the tape, which can be affixed to the outside of a face mask. The thermistor 103 can be located in an open hole that seals to the porous mask surface, maintaining mask integrity. A portion of the air passing through the face mask would pass over the thermistor allowing for detection as previously discussed. The tape mounting could include an adhesive that allows the mounting to be reused or can be a one-time disposable unit. One advantage of the tape mounting is that in addition to monitoring fit quality via flow history it can also enable quick and simple installation on the mask without specific training. It can also enable quick and simple installation on a mask without specific training required. FIG. 10E illustrates an example of the tape mounted system on a face mask. The tape mounted system can communicate information to a remotely located computing device (e.g., a user device such as tablet, smartphone, smartwatch, etc.) for processing and/or display. Note that in this mask application, other than sensing fit via flow history, sensing the expired air temperature could reveal a fever on the part of the wearer, possibly symptomatic of Covid-19.

Miniaturization. Given the operating method, sensor size reduction can improve performance in multiple ways: faster speed of response to equilibrium signal levels, more compact size for wearing comfort, and lower power consumption for longer battery lifetime. Utilizing a MEMS (microelectromechanical system on silicon) form of the sensing system can offer these improvements. Measurement of breath humidity can also be combined in a MEMS package that can allow a direct reference compensation relative to $CO_2$ for the disclosed methodology. MEMS-scale sensors that measure humidity, based on tin oxide, are available (see, e.g., "Humidity Sensors: A Review of Materials and Mechanisms" by Chen et al., *Sensor Letters, Vol.* 3, pp. 274-295, 2005).

Ambient air quality parameters contained within inhaled air. This disclosure has described measurements of instantaneous, maximum, and average breath velocities of exhaled breath. So, when affixed to the exterior surface of a porous mask, the trend of these dynamic values over time can reflect the rate of accumulation of particulate loading and thus levels of suspended particulate matter captured by the mask filter media from ambient air. Position data communicated from many masks can relate the particulate micro environmental conditions over time and locations. The relevant individual filtering media specifications will be a factor in these calculations.

The measurement of trace airborne molecular species inhaled within the ambient air may also be achieved. Thermistors can be made from semiconductor materials, typically metallic oxides such as, e.g., cobalt, manganese, or nickel. In addition to sensing water vapor, $SnO2$ can be used for multiple gases, especially harmful oxides such as $NO_2$, CO and $PbO_2$. Different contact and monitoring arrangements make it possible to discriminate between different contributions to the overall conduction in $SnO_2$. For example, a band scheme and equivalent circuits can be used for electrical characterization of different components (see, e.g., "A.C. Measurements of tin oxide sensors to improve selectivity and sensitivities" by Weimar et al., *Sensors and Actuators B; Chemical*, Vol. 26, Issues 1-3, pp. 13-18, 1995). Since these sensors are operated at temperatures above 200 C, heaters can be attached at the backside. Control algorithms and computations associated with MEMS systems can be configured to elicit this useful data and extend utility to harvesting multi-point profiles of environmental pollutants. This would be of value both to the mask-wearer and the general wider population.

Figure 11A:
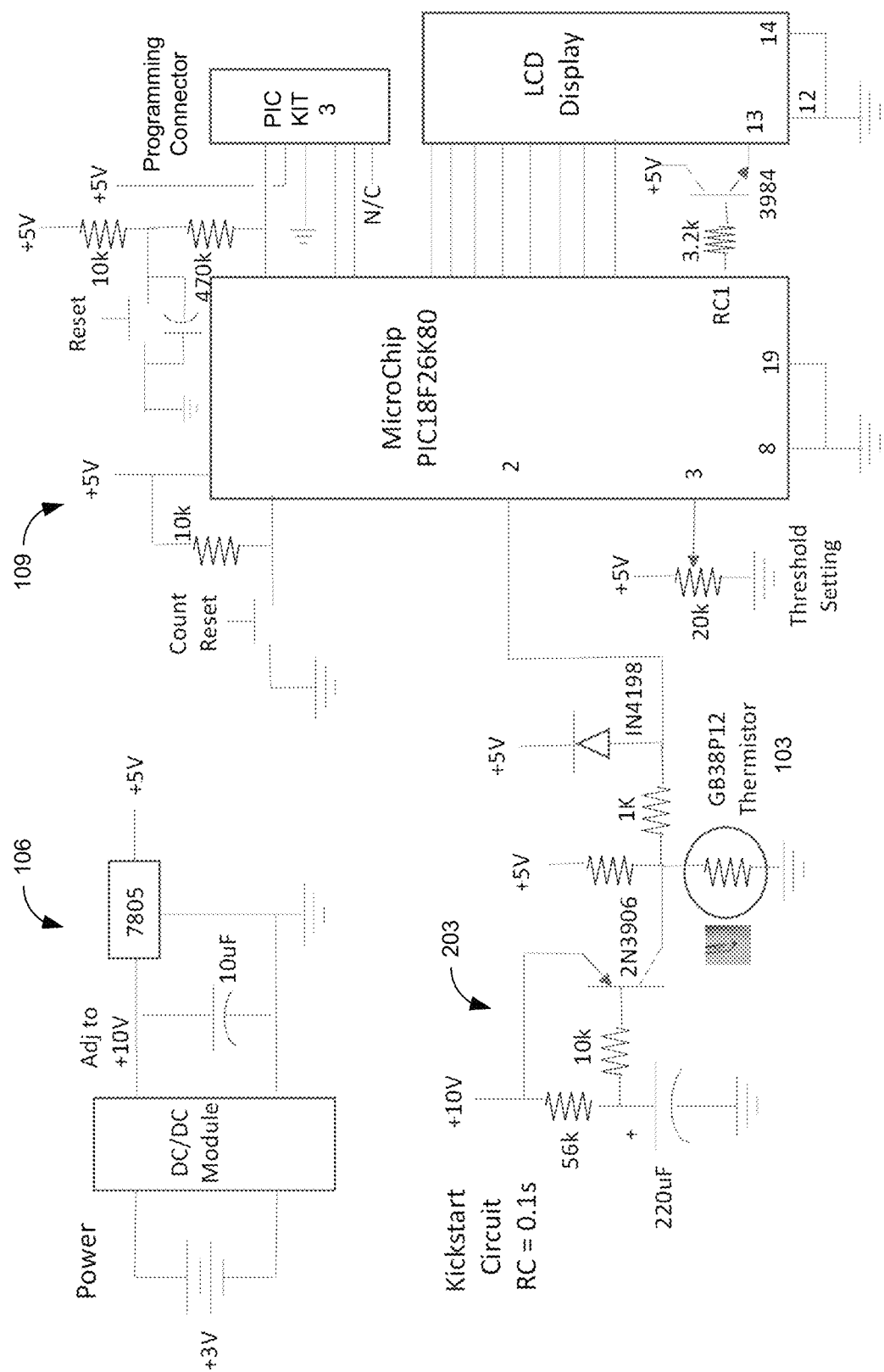
FIGS. 11A-11C are schematic diagrams illustrating examples of sensing and control circuitry for thermistor based respiration measurement, in accordance with various embodiments of the present disclosure.
Figure 11B:
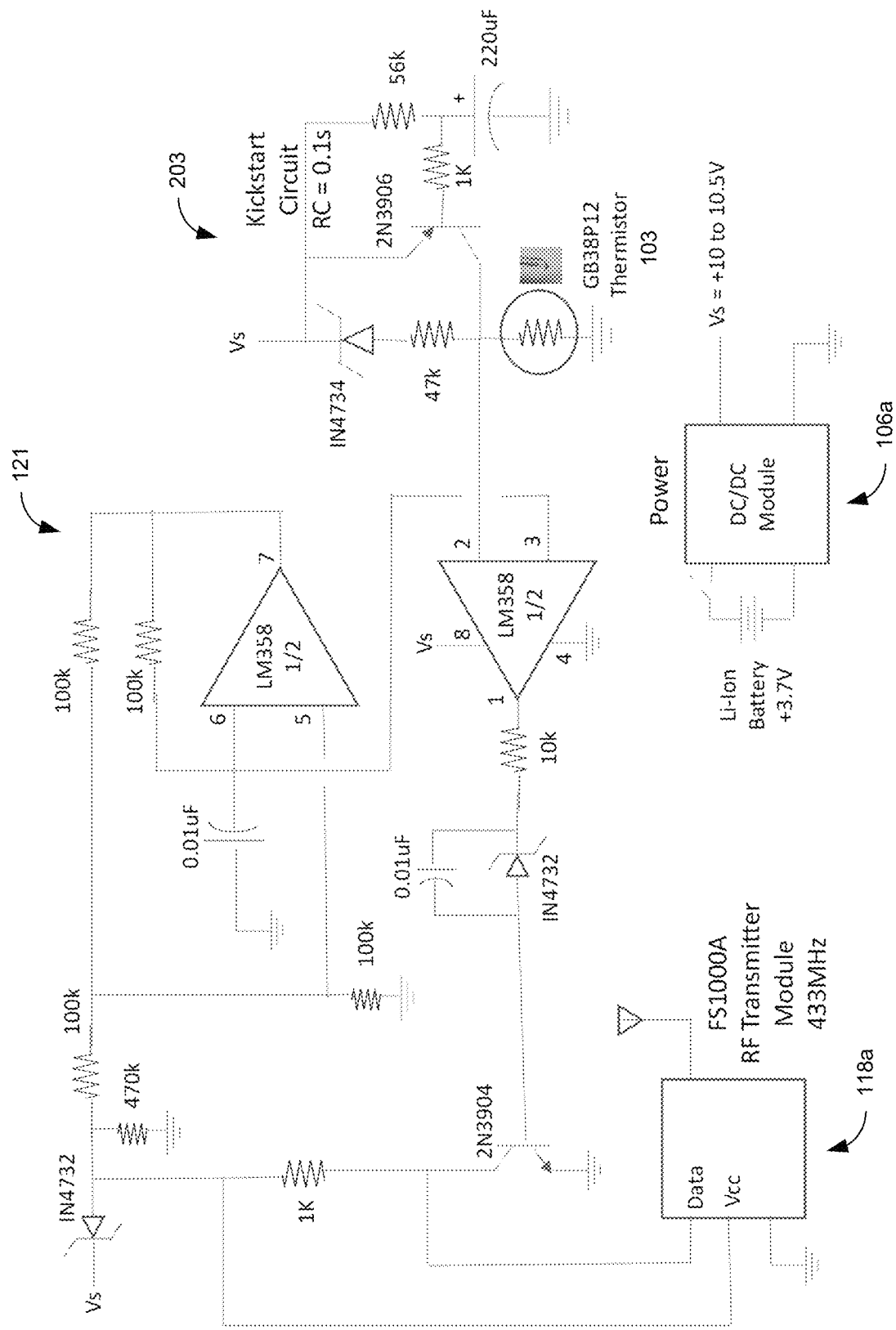
Figure 11C:
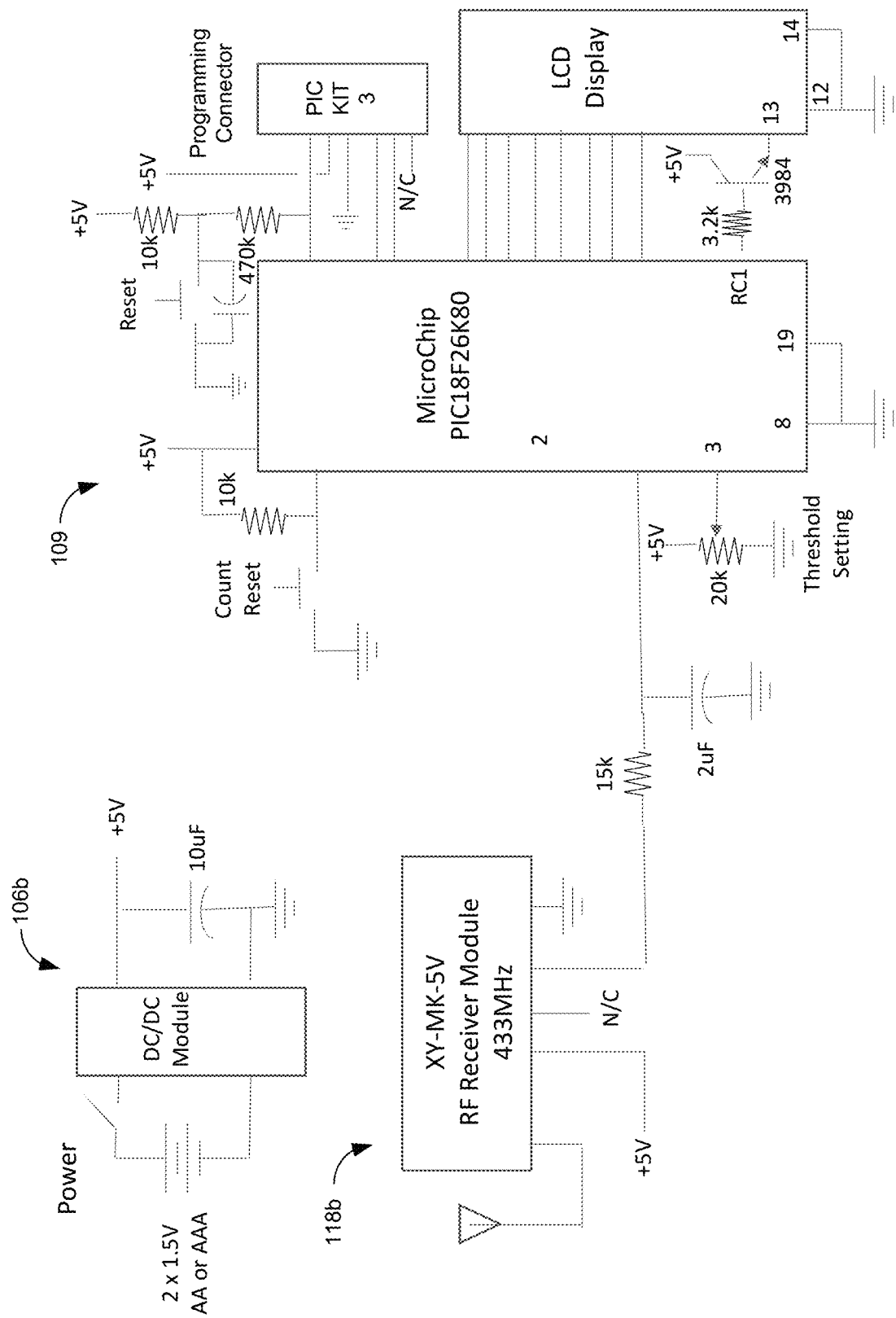

Referring now to FIGS. 11A-11C, shown are examples of sensing and control circuitry for thermistor based respiration measurement. FIG. 11A shows an example of respiratory measurement circuitry utilizing a single thermistor 103 with a hardwire connection to the intelligent control and processing circuitry 109. A startup circuit 203 that can be operated to trigger the thermistor 103 into a self-heat mode. A voltage supply 106 can include a DC/DC module configured to step up battery voltage to a level needed by the sensing and control circuitry. The transistor can be activated to start the thermistor heating and is deactivated after a predefined heating period, e.g., by an RC timing circuit on the base of the transistor. In the example of FIG. 11A, no switching circuitry in included to switch to a temperature sensing mode, thereby reducing the complexity of the design.

The intelligent control and processing circuitry 109 can be configured to monitor the thermistor 103 during the sensing modes. A microchip or microprocessor can continuously monitor the voltage across the thermistor 103 during the switching to determine one or more variables such as, e.g., breath temperature, breathing rate, maximum breath velocity, single-breath volume (in and out), or $O_2$ to $CO_2$ respiration efficiency. The intelligent control and processing circuitry can include a display to provide indications of the determined variable(s). A connector (PICKIT3) can facilitate programming or setup of the microchip or microprocessor.

FIGS. 11B and 11C show an example of respiratory measurement circuitry utilizing a single thermistor 103 with a wireless connection (e.g., Bluetooth® or other appropriate RF link) to the intelligent control and processing circuitry 109. FIG. 11B shows sensing circuitry coupled to the thermistor 103. A startup circuit 203 that can be operated to trigger the thermistor 103 into a self-heat mode. A voltage supply 106a can include a DC/DC module configured to step up battery voltage to a level needed by the sensing and transmitting circuitry. A radio frequency (RF) transmitter (or transceiver) 118a can transmit the monitored data provided via conditioning circuitry 121 to remotely located receiving circuitry for processing. Circuitry 121 converts the raw sensor analog value to a PWM (pulse width modulated) form, which is provided to the RF transmitter (or transceiver) 118a for wireless transmission by, e.g., variable pulse width modulation.

FIG. 11C shows an example of the remotely located receiving circuitry configured to process the data transmitted from the sensing circuitry of FIG. 11B. A voltage supply 106b can include a DC/DC module configured to step up battery voltage to a level needed by the receiving and processing circuitry. A RF receiver (or transceiver) 118b can receive the monitored data from the remotely located sensing circuitry for processing. The intelligent control and processing circuitry 109 can comprise a microchip or microprocessor that can determine one or more variables such as, e.g., breath temperature, breathing rate, maximum breath velocity, single-breath volume (in and out), or $O_2$ to $CO_2$ respiration efficiency from the received data. The intelligent control and processing circuitry can include a display to provide indications of the determined variable(s). In other implementations, a user device such as a smart phone, tablet or other computing device can be used as the receiving and processing circuitry.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The term "substantially" is meant to permit deviations from the descriptive term that don't negatively impact the intended purpose. Descriptive terms are implicitly understood to be modified by the word substantially, even if the term is not explicitly modified by the word substantially.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 V % to about 5 V %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A breath sensing system, comprising:
    a self-heating temperature sensor configured to be positioned in respiratory air of a subject;
    electronic switching circuitry operably connected to the self-heating temperature sensor, the electronic switching circuitry configured to change operation of the self-heating temperature sensor between a temperature sensing mode and a heated power dissipation sensing mode, where either the temperature sensing mode or the heated power dissipation sensing mode is selected to operate during bidirectional respiration or a quiescent period of the subject; and processing circuitry configured to monitor operation of the self-heating temperature sensor and control switching between the temperature sensing mode and the heated power dissipation sensing mode, where the processing circuitry is configured to communicate respiratory information associated with physical or physiological properties of the subject to a remotely located computing device.

2. The breath sensing system of claim 1, wherein the self-heating temperature sensor is a thermistor.

3. The breath sensing system of claim 1, wherein the respiratory information is associated with breath temperature, breath velocity, breath period, breath inhalation volume, breath exhalation volume, breath carbon dioxide level, heart rate, or combinations thereof.

4. The breath sensing system of claim 1, wherein the self-heating temperature sensor is heated to a defined temperature when the electronic switching circuitry is switched to the heated power dissipation sensing mode.

5. The breath sensing system of claim 4, wherein the processing circuitry monitors, while in the heated power dissipation sensing mode, power demand of the self-heating temperature sensor during the bidirectional respiration of the subject.

6. The breath sensing system of claim 5, wherein the processing circuitry is configured to determine breath velocity, breath volume or breath carbon dioxide level based at least in part upon the monitored power demand.

7. The breath sensing system of claim 6, wherein the determined breath volume is breath inhalation volume or breath exhalation volume.

8. The breath sensing system of claim 6, wherein the breath carbon dioxide level is determined based at least in part upon power demand during quiescence or exhaling.

9. The breath sensing system of claim 1, comprising a power source electrically coupled to the electronic switching circuitry.

10. The breath sensing system of claim 1, wherein the electronic switching circuitry comprises a startup circuit configured to initiate self-heating of the self-heating temperature sensor by energizing the self-heating temperature sensor at an increased voltage level for a predefined heating period.

* * * * *